United States Patent [19]

Walker et al.

[11] Patent Number: 5,015,799

[45] Date of Patent: May 14, 1991

[54] OXIDATIVE COUPLING PROCESS FOR CONVERTING METHANE AND/OR NATURAL GAS TO MORE TRANSPORTABLE PRODUCTS

[75] Inventors: Robert H. Walker, Chicago; Paul A. Willems, Geneva; George A. Huff, Naperville; Lewis E. Grimes, Oak Park; David F. Tatterson, Downers Grove; Robert L. Mehlberg, Wheaton, all of Ill.

[73] Assignee: Amoco Corporation, Chicago, Ill.

[21] Appl. No.: 376,307

[22] Filed: Jul. 6, 1989

[51] Int. Cl.$^5$ .............................................. C07C 2/00
[52] U.S. Cl. .................................... 585/500; 585/661; 585/943; 585/750; 585/660; 585/654; 585/656; 585/658; 585/541; 585/415
[58] Field of Search ............... 585/500, 661, 943, 750, 585/660, 654, 656, 658, 541, 415

[56] References Cited

U.S. PATENT DOCUMENTS 4,205,194 5/1980 Mitchell, III et al. .............. 585/500
4,499,324 2/1985 Gaffney ................................ 585/500
4,654,459 3/1987 Sofranko ............................. 585/943
4,822,940 4/1989 Leff et al. ........................... 585/500

FOREIGN PATENT DOCUMENTS 0178853 4/1986 European Pat. Off. .

OTHER PUBLICATIONS

Keller et al., "Synthesis of Ethylene via Oxipative Coupling of Methane", *Joxcatalysis*, 73, pp. 9–19, (1982).

*Primary Examiner*—Patrick P. Garvin
*Assistant Examiner*—E. D. Irzinski
*Attorney, Agent, or Firm*—Nick C. Kottis; William H. Magidson; Ralph C. Medhurst

[57] ABSTRACT

A method for converting methane to higher molecular weight hydrocarbons wherein hot oxidative coupling reactor effluent is briefly contacted with a $C_2$ to $C_{20}$ alkane quench material to remove part of the heat contained in the raw reactor effluent, and is then further quenched by thermal quenching means to achieve a temperature which discourages retrograde reactions.

29 Claims, 1 Drawing Sheet

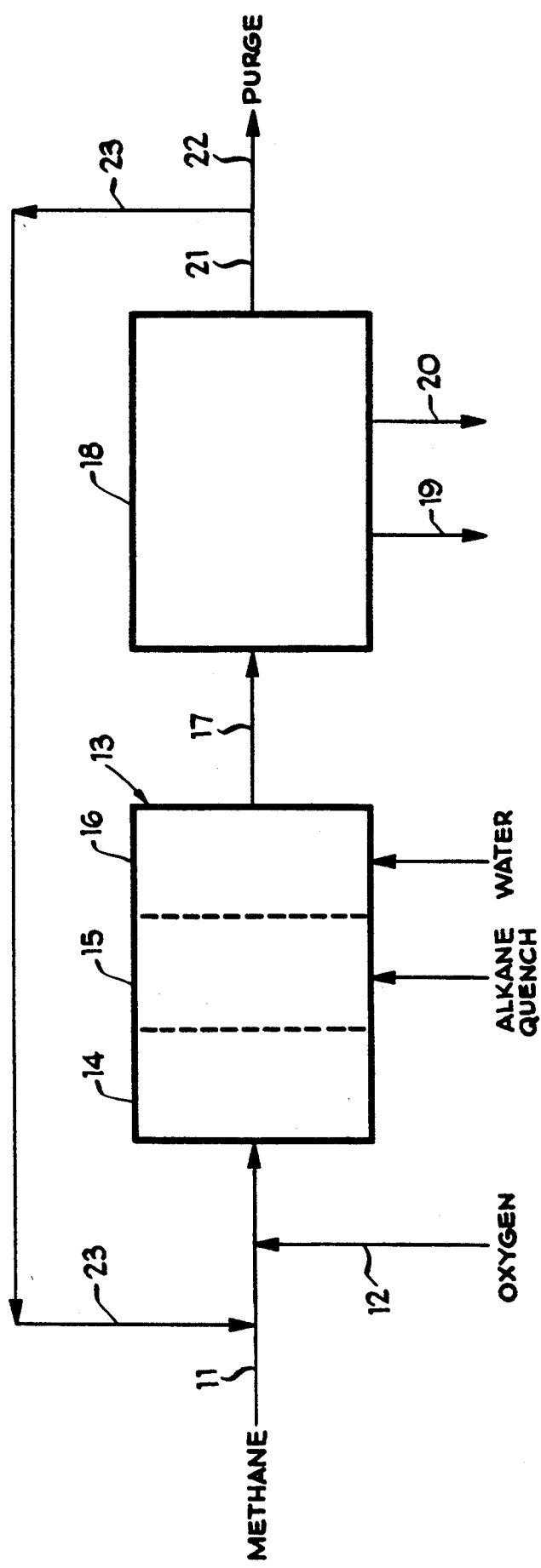

OXIDATIVE COUPLING PROCESS FOR CONVERTING METHANE AND/OR NATURAL GAS TO MORE TRANSPORTABLE PRODUCTS

FIELD OF THE INVENTION

This invention relates to an improved oxidative coupling process for converting methane and/or natural gas to liquid higher molecular weight products which are more readily transportable from the field, and more particularly relates to a process wherein high quality heat wasted in prior art processes is captured, and additional hydrogen is provided for use in converting low value carbon oxides to more valuable products.

BACKGROUND OF THE INVENTION

A major source of methane is natural gas which typically contains about 40-95% methane depending on the particular source. Other constituents include about 10% ethane with the balance being made up of $CO_2$ and smaller amounts of propane, butanes, pentanes, nitrogen, etc.

Primary sources for natural gas are reservoirs either alone or generally associated with hydrocarbon liquid reserves. Most of the natural gas used for heating purposes comes from these sources. Quantities of natural gas are also known to be present in coal deposits and are by-products of crude oil refinery processes and bacterial decomposition of organic matter.

Prior to commercial use, natural gas must be processed to remove water vapor, condensible hydrocarbons and inert or poisonous constituents. Condensible hydrocarbons are generally removed by cooling natural gas to a low temperature, and then washing it with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, butanes, pentanes, carbon dioxide and nitrogen. Generally, processed natural gas comprises from about 70% to more than about 95% by volume of methane.

Most processed natural gas used commercially is distributed through extensive pipeline distribution networks. As natural gas reserves in close proximity to gas usage decline, new sources that are more remote require transportation over further distances. The gas from many of these distant sources is not, however, amenable to transport by pipeline. For example, the gas from sources that are located in areas requiring economically unfeasible pipeline networks, or in areas requiring transport across large bodies of water, is not amenable to transport by pipeline. This problem has been addressed in several ways. One such solution has been to build a production facility at the site of the natural gas deposit to manufacture one specific product. Another approach has been to liquefy the natural gas and transport it in specially designed tanker ships. Natural gas can be reduced to 1/600th of the volume occupied in the gaseous state by cryogenic processing, and with proper procedures, safely stored or transported. These processes, which involve liquefying natural gas, transporting the liquified gas, and revaporizing it are complex, energy intensive and expensive.

Still another approach has been the conversion of natural gas to higher molecular weight hydrocarbons or oxygenates, preferably substantially liquid hydrocarbons or oxygenates, that can be easily handled and transported. The conversion of natural gas to higher order hydrocarbons, especially ethane and ethylene, retains the material's versatility for uses as precursor materials in chemical processing. Known dehydrogenation and polymerization processes are available for the further conversion of ethane and ethylene to liquid hydrocarbons. In these ways, easily transportable commodities may be derived from natural gas at the wellhead. A drawback in implementing such processes has been the lack of means for obtaining a sufficiently economical conversion rate of natural gas to higher molecular weight hydrocarbons.

The conversion of methane to higher molecular weight hydrocarbons at higher temperatures, in excess of about 1200° C., is known. These processes are, however, energy intensive and have not been developed to the point where high yields are obtained even with the use of catalysts. Some catalysts or promoters that are useful in these processes, e.g. chlorine, are corrosive under such operating conditions.

Low temperature reactions, e.g. 250° C. and 500° C., of hydrocarbon feedstocks to higher molecular weight hydrocarbons are described in U.S. Pat. Nos. 4,433,192; 4,497,970 and 4,513,164. The processes described in these patents utilize heterogeneous systems and solid acid catalysts. In addition to the solid acid catalysts, the reaction mixtures described in the -970 and -164 patents include oxidizing agents. Among the oxidizing agents disclosed are air, $O_2$-$O_3$ mixtures, S, Se, $SO_3$, $N_2O$, NO, $NO_3$, F, etc.

One area of active interest has been labelled oxidative coupling, and generically consists of promoting the following reaction:

Natural 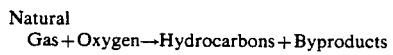
Gas + Oxygen → Hydrocarbons + Byproducts where Natural Gas is used to represent natural gas or its components, Oxygen is used to represent either molecular or chemically bound oxygen, Hydrocarbons is used to represent species containing more than one carbon atom, and Byproducts represents water, carbon oxides and solid carbonaceous materials. Proposed configurations for accomplishing the above reaction vary, including cofeed, where oxygen and methane are mixed and reacted either directly or in the presence of a catalyst, and redox, where a solid ferries oxygen from one vessel (generator) to another (reactor) in which the desired oxidative coupling takes place. Many examples of these configurations exist in the patent and technical literature, including numerous patents by Exxon, Atlantic Richfield, Chevron, ARCO Chemical Company and others.

See for example, U.S. Pat. Nos. 4,754,093; 4,751,336; 4,704,496; 4,613,426; 4,599,478; 4,599,479; 4,587,001; 4,556,749; 4,527,002; 4,527,003; 4,520,224; 4,430,096; 4,288,408; and 3,900,525.

The catalytic oxidative coupling of methane at atmospheric pressure and temperatures of from about 500° C. to 1000° C. has been investigated by G.E. Keller and M.M. Bhasin. These researchers reported the synthesis of ethylene via oxidative coupling of methane over a wide variety of metal oxides supported on an alpha-alumina structure in *Journal of Catalysis*, 73, 9–19 (1982). This article discloses the use of single component oxide catalysts that exhibited methane conversion to higher order hydrocarbons at rates no greater than 4%. The process by which Keller and Bhasin oxidized methane was cyclic, alternating the feed composition between methane and nitrogen and air (oxygen) to obtain higher selectivities.

The conversion of methane to higher molecular weight hydrocarbons using metal oxide catalysts and oxides of carbon, which are generated from the hydrocarbon, is also described in U.S. Pat. No. 2,180,672. The conversion generally is carried out at temperatures of from about 150°-350° C., and the oxides of carbon are consumed in the reaction.

U.S. Pat. No. 1,677,363 describes the conversion of methane or natural gas to ethylenic hydrocarbons by heating a thin stream of methane or natural gas to a temperature not exceeding 950° C. U.S. Pat. No. 4,304,657 describes a process for converting feedstocks comprising aliphatic fractions boiling at 70° C. Typically, the feedstock may be naphthas, coker gasolines, FCC gasoline, and pyrolysis gasolines. The process uses aromatization catalysts and a diluent which may be $CO_2$, CO or nitrogen, and the dilution is in a molar ratio of diluent to feed of from about 20:1 to 1:1. Preferred dilutions are 10:1 to 5:1 of diluent to feed.

Methods for converting methane to higher molecular weight hydrocarbons at temperatures in the range of about 500° C. to about 1000° C. are disclosed in U.S. Pat. Nos. 4,443,644; 4,443,645; 4,443,646; 4,443,647; 4,443,648 and 4,443,649. The processes taught by these references provide relatively high selectivities to higher order hydrocarbons, but at relatively low conversion rates, on the order of about less than 4% overall conversion. In addition to synthesizing hydrocarbons, the processes disclosed in these references also provide a reduced metal oxide which must be frequently regenerated by contact with oxygen. The preferred processes of these references entail physically separate zones for a methane contacting step and for an oxygen contacting step, with the reaction promoter recirculating between the two zones.

U.S. Pat. Nos. 4,172,810; 4,205,194; and 4,239,658 disclose the production of hydrocarbons including ethylene, benzene, ethane, propane, and the like in the presence of a catalyst-reagent composition which comprises: (1) a group VIII noble metal having an atomic number of 45 or greater, nickel or a group Ib noble metal having an atomic number of 47 or greater; (2) a group VIb metal oxide which is capable of being reduced to a lower oxide; and (3) a group IIa metal selected from the group consisting of magnesium and strontium composited with a passivated, spinel-coated refractory support or calcium composited with a passivated, non-zinc containing spinel-coated refractory support. The feedstreams used in the processes disclosed in these patents do not include gaseous oxygen. Oxygen is excluded for the purpose of avoiding the formation of carbon oxides from useful intermediate hydrocarbon compounds. Oxygen is generated for the reaction from the catalyst, thus requiring periodic regenerations of the catalyst.

U.S. Pat. No. 4,450,310 discloses a methane conversion process for the production of olefins and hydrogen comprising contacting methane in the absence of oxygen and in the absence of water at a reaction temperature of at least 500° C. with a catalyst comprising the mixed oxides of a first metal selected from the group consisting of lithium, sodium, potassium, rubidium, cesium and mixtures thereof; a second metal selected from the group consisting of beryllium, magnesium, calcium, strontium, barium, and mixtures thereof; and optionally, a promoter metal selected from the group consisting of copper, rhenium, tungsten, zirconium, rhodium, and mixtures thereof.

In general, the oxidative coupling processes operate at moderately high temperatures, typically 600°-1000° C. in catalytic systems, and temperatures in excess of 1000° C. in non-catalytic systems, and characteristically have conversions per pass of 1-40 percent of the contained methane. Selectiveness to the $C_2+$ products or intermediates range from 20-90+ percent. In general, if a catalyst is run to maximize selectivity, it will exhibit lower conversion, and running under conditions that increase conversion results in a reduction in selectivity.

The combination of moderate conversion per pass and the characteristic production of quantities of excess carbon oxides obtained in the prior art processes limits the utility of present oxidative coupling approaches. Particularly important is the tendency of both the catalytic and non-catalytic systems to produce significant quantities of carbon oxides which are of relatively low value. Increasing levels of conversion per pass usually increases the problem of carbon oxide production.

Some of the selectivity loss can be recaptured by reacting any hydrogen produced in the process with some of the co-produced carbon oxides to manufacture oxygenates or, directly or indirectly, higher hydrocarbons. However, much of the hydrogen is usually converted to water and is unavailable for the conversion of carbon oxides to useful products. In general, carbon oxide conversion can increase useful product yields by up to 3% based on previously published yield structures.

An equally important limitation in prior art processes is the necessity of running the oxidative coupling reaction at elevated temperatures, and then rapidly cooling or quenching the reactor product to reduce the occurrence of severe retrograde reactions. Typically the temperature of the reactor effluent must be lowered to 700° C. or even 600° C. to reduce the formation of carbonaceous deposits, the hydrogenation of produced olefins to lower value aliphatic compounds, etc. This temperature reduction generally is accomplished in from less than one second to a few seconds by quenching with water or other heat absorbing medium. This approach has major drawbacks which the present invention overcomes. Specifically, valuable high quality (high temperature) heat is wasted, and low quality (low temperature) heat, which must then be disposed of at significant cost, is increased. Further, at attractive selectivities to desired intermediate or end products, the present state of the art provides, at best, approximately 25% conversion rate. In view of the low conversion rates, coupled with the other drawbacks discussed above, there remains a need for an efficient, cost effective, improved method of converting methane to higher hydrocarbons via oxidative coupling. The present invention provides such a process.

Thermal or physical quenching has heretofore been employed in prior art cracking processes involving gross volumes of heavy hydrocarbon feeds where heat is fed into the system to promote feedstock cracking, after which the reaction is quenched to prevent retrograde reactions. Generally speaking, prior art processes that employ hydrocarbons as a heat sink are doing so as a mechanism to reduce process stream volume and the size of heat recovery equipment downstream which is required if water vaporization is used to absorb heat and lower stream temperatures. Such prior art techniques, however, including equipment are those described in U.S. Pat. Nos. 4,520,224, 4,288,408, 4,556,749 and 4,384,160, all rely on specific heat capacity, phase change, heat of vaporization, and the like to dilute the concentration of heat thus lowering stream temperature. These prior art processes produce lower quality heat downstream resulting in the requirement of more heat rejection equipment in the form of cooling towers, vaporizers, heat exchangers and the like. Further, the prior art cracking processes which inadvertently employ some form of chemical quenching, that is, use a chemical agent to achieve a thermal or physical quench, as opposed to a true chemical quench as employed in the present invention, produce methane in a form only useful as process fuel, the very material the present invention is designed to convert to more transportable, higher hydrocarbons.

In the present invention, on the other hand, high quality heat is absorbed in the upgrading of the quench material to a useful product or intermediate. In addition, hydrogen produced as a result of the conversion of the quench material can be used to convert otherwise low value or waste carbon oxides to desired products or intermediates.

Thus, the present invention overcomes drawbacks of the prior art and improves the economic feasibility of both catalytic and non-catalytic oxidative coupling processes, including both cofeed and redox configurations, by recapturing the high quality heat wasted in the prior art processes, and by providing additional hydrogen which can be used to convert low value or waste carbon oxides to more valuable products.

SUMMARY OF THE INVENTION

The oxidative coupling process of this invention comprises a method for converting methane to higher molecular weight hydrocarbons by reacting a methane containing feedstock with an oxygen-containing material in a reaction zone of an oxidative coupling reactor to produce an effluent stream comprising $C_2+$ hydrocarbons; and removing heat from the effluent stream by briefly contacting hot coupling reactor effluent with a $C_2-C_{20}$ alkane quench material having a temperature of up to 1000° C. to produce a chemically quenched stream wherein part of the heat contained in the raw reactor effluent gas been removed. The temperature of the chemically quenched effluent stream is further reduced by thermal means, using, for example, water, recirculating refractory oils, a heat exchanger, or other heat absorbing means a achieve a temperature which discourages or retards retrograde reactions.

More particularly, the process of the present invention provides a method for converting a methane rich feedstock to higher molecular weight hydrocarbons comprising the steps of: reacting the feedstock with an oxygen-containing material in a reaction zone of an oxidative coupling reactor to produce an effluent stream comprising $C_2+$ hydrocarbons; and introducing an alkane quench material having a temperature of up to 1000° C. to produce a chemically quenched effluent stream having a reduced temperature. Thereafter, the process of this invention may comprise the additional steps of further reducing the temperature of the chemically quenched stream by thermal means to retard retrograde reactions; and separating and removing $C_2+$ hydrocarbon and carbon oxide products from the product stream. If desired, at least a portion of unreacted methane, unreacted alkane quench material, alkanes formed during chemical quenching, and mixtures thereof contained in the product stream may be recycled to the reaction zone. In addition, at least a portion of the $C_2+$ hydrocarbons may be reacted to form higher homologs and oxygenates.

$C_2+$ hydrocarbons may be separated and removed from unreacted methane either from the effluent stream following the chemical quench or from the product stream following the thermal quench.

The process may be advantageously conducted in the presence of an oxidative coupling catalyst in the reaction zone.

The intermediate hydrocarbon quench provides a number of major benefits. First, it absorbs some of the heat otherwise removed by wasteful techniques through an extremely fast endothermic reaction. Second, at least a portion of the hydrocarbon quench is converted to reactive intermediate or valuable end products. A further advantage is the production of additional hydrogen that can be used to improve the value of end products or increase yields by converting carbon oxides to valuable products or intermediates.

It is presently preferred to employ the process of this invention in the vicinity of a gas extraction plant. Ethane, propane, butanes, other natural gas liquids, condensates, etc., which are presently several of the preferred quench media for use in the gasifier, can be isolated at low cost in many gas plants. Furthermore, in remote locations where methane conversion technologies are likely to be implemented, these components usually have a low value and are expensive to transport to markets.

BRIEF DESCRIPTION OF THE DRAWING

FIG. 1 shows a process flow scheme for a representative oxidative coupling process in accordance with this invention.

DETAILED DESCRIPTION OF THE INVENTION

Referring to FIG. there is depicted one preferred embodiment in which oxidative coupling and quench operations are accomplished in different zones of a reaction vessel. Other configurations for contacting hot reaction gases with hydrocarbon quench materials, such as separate units, may be employed.

Methane, illustrative of a feedstock such as natural gas, is introduced into the system by line 11 where it is mixed with oxygen, air, or other oxygen-source gas supplied through line 12. The resulting mixture is fed into a first zone 14 of oxidative coupling reactor 13 where it is contacted with oxidative coupling catalyst for conversion to higher hydrocarbons. The hot gaseous feedstream passes on to hydrocarbon quench zone 15 where it is mixed and reduced in temperature by the introduction of alkane quench material, after which the reactor stream progresses to final quench zone 16 at which point a diluent such as water is introduced to further cool the stream and prevent retrograde reactions.

Depending on the level of temperature reduction and downstream processing desired, several alternative flow configurations may be used, two of which are described below. If the effluent is cooled below the condensation point of water, the reactor effluent passes through line 17 into product separator 18 where some $C_2+$ hydrocarbon product and water, $H_2$ and carbon oxides ($CO_x$ wherein x is 1 or 2) byproducts are withdrawn through lines 19 and 20. The stream is then cooled to recover $C_2+$ products. The remainder of the stream passes out of the separator into line 21 where the gaseous effluent is divided, with a portion of the effluent being recycled in line 23 as feedstock back into the reactor and the minor portion being removed from the system by purge line 22.

If desired, the process flow scheme depicted in FIG. 1 may be changed to allow for the production of intermediates, the incorporation of carbonylation, hydroformylation, carbon oxide hydrogenation and other processes known to those skilled in the art to produce derivative products.

The hydrocarbon quench employed in the practice of this invention is preferably a $C_2-C_{20}$ straight or branched chain alkane.

The term "$C_2-C_{20}$ alkane", as used herein, refers to a straight or branched-chain alkane, e.g., ethane, propane, n-butane, 2-methylpropane, n-pentane, 2-methylbutane, 2,2-dimethylpropane, n-hexane, 2-methylpentane, 2,3-dimethylbutane, n-heptane, 2,3-dimethylpentane, n-octane, 3-ethyl-2,3-dimethylhexane, n-dodecane, n-octadecane, n-eicosane, and the like. Suitable quench materials also may include naphthas.

The term "naphthas", as used herein, refers to hydrocarbon product mixtures that distill at a boiling range below 180°–190° C.

It is preferred to employ paraffinic hydrocarbons as the quench material, more particularly light alkanes, i.e. $C_2-C_5$ alkanes. However, the presence of moderate amounts of aromatics, while not desirable, would not be detrimental to the process of this invention. Rather, aromatics would serve as diluents. However, naphthenic components are not desirable since they have a lesser tendency to produce desirable olefins. The term "naphthenes" or "naphthenic components" refers to multiringed compounds containing both aromatic and saturated rings, also referred to as cycloalkylaryl compounds.

The term "chemical quench", as used herein, refers to a means for reducing the temperature of the effluent stream in which the quench material itself is also chemically modified to provide desirable materials.

It is especially preferred to employ light hydrocarbons, preferably $C_2-C_5$ alkanes, in the practice of this invention. However, as a practical matter, the actual selection of the hydrocarbon quench material will depend upon what is available in the field. Varying the selection of the alkane will vary the product distribution; however, regardless of the alkane available, the end products will be in the desired range.

Generally speaking, the alkane quench comprises from 1 to 25 weight percent of the process stream just prior to the alkane quench addition, preferably from 5 to 20 weight percent and most preferably from 10–20 weight percent. The exact amount of quench material used will depend on the volume and composition of the quench material available, the conditions at which the oxidative coupling segment is run, and the desired downstream composition.

The alkane quench material may be employed at ambient temperature, but is preferably heated to temperatures of up to 1000° C. It is preferred to heat the quench material to temperatures of from 200°–800° C., and most preferably to a temperature of from 500°–700° C. In cases where there is a cryogenic unit at the site, temperatures as low as −150° C. may be employed. However, for best results, it is preferred to introduce the alkane quench material into the oxidative coupling reactor at elevated temperatures as discussed above, most preferably, if feasible, at the temperature of the effluent stream. The optimum preheat temperature will be governed by the composition of the quench, and process conditions upstream and downstream of the quench operation. The upper limitation on the temperature of the quench material is the thermal stability of the material. This will, in part, depend upon whether or not the material is diluted and the diluent. For example, if a quench material is diluted with carbon dioxide, steam or other diluents, it may be heated to a higher temperature without degrading.

The process of this invention may be run under a wide range of pressures, i.e. atmospheric to 500 psi. It is preferable to operate at pressures of at least 5 psi, more preferably, from about 15 psi to 300 psi, and most preferably from about 20 to about 200 psi.

The temperature at which the oxidative coupling reaction is run will depend upon the type of reactor, and the catalyst employed. Generally speaking, in the case of a cofeed operation, the temperature should be maintained at from about 600°–1100° C., depending upon the particular catalyst and equipment employed.

It is critical that the temperature of the effluent stream leaving the reactor be maintained at a minimum of 600° C., and preferably not drop below 700° C. for best results.

The use of an alkane chemical quench, immediately followed by a thermal quench results in extremely short effective contact times, on the order of from a few milliseconds to less than 1.5 seconds, since heat transfer is not limited either on heating or cooling by the resistance of tube walls as is the case in conventional ethylene production units. This residence time is critical. It is critical that the alkane quench contact time be as brief as possible, preferably under 2 seconds, i.e. from 0.02 to 2 seconds. It is believed that all reaction occurs in under 1.5 seconds, with most of the reaction occurring in milliseconds, i.e. 0.02–0.5 second, and it is preferred that residence time not exceed 1.5 seconds. The residence time of the alkane quench material within the reactor will depend upon the configuration of the reactor and other conditions which are well known and within the skill of the art.

The process of this invention may be employed in both cofeed and redox reactions.

A wide range of oxidative coupling catalysts may be employed in the practice of this invention. Many commercially available catalysts which have been used in different processes are suitable for use in the present invention. The word "catalyst", as used herein, includes a material which promotes or strongly affects the rate of a chemical reaction but itself remains unchanged, as well as materials which are oxygen-carrying substances which strongly affect the rate of a chemical reaction, and which themselves may undergo transient chemical change in their oxidative state, and materials which may be altered physically by chemically absorbed molecules of the reactants and reaction products. It is also understood that the catalyst employed in this invention may be formed in situ. For example, in the present invention when an oxide, nitride, or carbide metal catalyst is initially charged to the reactor, the oxide and nitride may be converted in situ to the carbide which then functions as the catalytic species.

Catalysts used in the practice of this invention may be used with or without catalyst supports.

For example, a metal-containing catalyst comprising a reducible compound of lead, antimony, germanium, vanadium, tin, bismuth, cadmium, indium, manganese, thallium or a mixture thereof may be employed in the practice of this invention. The reducible compound employed may be an oxide, sulfate or carbonate of lead, antimony, germanium, vanadium, tin, bismuth, cadmium, indium, manganese, thallium, or a mixture thereof.

The oxidative coupling catalyst employed in this invention may comprise, in addition to the aforesaid reducible metal compound, an amorphous refractory inorganic oxide support comprising an oxide of an element from Group IIa, IIIa, IIIb, IVa or IVb of the Periodic Table. The inorganic oxide support may be, for example, silica, alumina, silica-alumina, silica-stabilized alumina, phosphated alumina, silica-stabilized phosphated alumina, alumina-aluminum phosphate, boria-alumina, magnesia-alumina, boria, magnesia or titania.

The reducible compound component on the support component of the oxidative coupling catalyst can comprise from about 2 to about 50 weight percent of the catalyst, calculated as the reducible metal oxide and based on the total weight of the catalyst. See U.S. Pat. No. 4,754,093.

An especially preferred catalyst for use in the present invention comprises a mixed oxide of: a) a Group IIIb metal cationic species selected from the group consisting of yttrium, lanthanum and scandium; b) a Group IIa metal cationic species selected from the group consisting of barium, calcium and strontium; and c) a Group IVa metal cationic species selected from the group consisting of tin, lead and germanium; and wherein the cationic species are present in the approximate molar or atomic ratio of 1:0.5-3:2-4, respectively.

In the case of a cofeed process, the reactionzone catalyst system can be either the fixed or fluidized bed type. The process is equally applicable, however, to redox systems.

The catalyst may also comprise silica having a surface area less than about 175 m²/gm such as that disclosed in U.S. Pat. No. 4,754,093. Also useful as catalysts in the present invention are those such as disclosed in U.S. Pat. No. 4,704,488.

Examples 1-3 show that cracking of alkanes in the quench stream takes place at process conditions of interest and that the desirable products in the reaction zone effluent do not seem to be adversely affected by the reactions or presence of the quench materials or by the chemical quenching process.

EXAMPLE 1

The composition of the oxidative coupling reactor effluent is set forth in Table I below.

| Component | Mole % |
|---|---|
| CO | 0.6 |
| $CO_2$ | 3.1 |
| $H_2$ | 3.4 |
| $H_2O$ | — |
| $CH_4$ | 85.9 |
| $C_2H_6$ | 2.8 |
| $C_2H_5$ | 2.7 |
| $C_3H_8 + C_3H_6$ | 0.2 |

-continued

| Component | Mole % |
|---|---|
| $N_2$ | 1.1 |

The reactor consisted of a stainless-steel jacket tube lined with an 11 mm OD (9 mm ID) quartz tube. A 3-mm quartz jacketed thermowell ran concentrically through the reactor. Inert alpha alumina filler (2.3 cc, 30-50 mesh) was packed in the middle of the rector tube to insure flow and temperature uniformity. The reactor tube was heated by a three-zone, 12 inch long furnace. The effective heated zone is assumed to be about 3 inches long which translates to a 4.3 cc reactor volume.

Effluent gas (stream "A") was introduced into the system at 100 sccm. In a control run, the reaction was run without any ethane cofeed. In subsequent runs, the effluent gas was blended with ethane (Stream "B") which was fed into the system through a separate feed line in the amount of 0, 5 or 10 sccm. Ethane was chosen for this run since it is the most refractory alkane other than methane. A water saturator was employed and the temperature of the saturator was adjusted to provide a water level of 5% in the blended effluent prior to its being fed into the reactor. Upon setting feed flow rates, samples of product stream "C" were taken for analysis by gas chromatography. Pressure was held constant at 1.5 atm. and temperature was varied from 600° to 850° C. in a manner to maintain an isothermal operation. At these conditions, the contact time of hot gases in the 4.3 cc volume was 1.1 sec.

The results of the control run are set forth in TABLE II.

TABLE II

Oxidative Coupling at 100 sccm and 1.5 atm
Without Ethane Cofeed

| Component | Feed-stream B (mole %) | Product Stream C (mole %) | | | | |
|---|---|---|---|---|---|---|
| | | 600° C. | 700° C. | 750° C. | 800° C. | 850° C. |
| Nitrogen | 1.09 | 1.06 | 1.14 | 0.99 | 1.03 | 0.97 |
| Hydrogen | 3.26 | 3.25 | 3.30 | 3.60 | 4.70 | 6.50 |
| CO | 0.62 | 0.66 | 0.89 | 0.75 | 0.63 | 0.72 |
| $CO_2$ | 2.95 | 2.94 | 2.92 | 2.88 | 2.88 | 2.82 |
| $H_2O$ | 5.44 | 5.57 | 5.96 | 7.20 | 6.27 | 6.84 |
| Methane | 81.19 | 81.08 | 80.38 | 79.35 | 79.32 | 77.41 |
| Ethane | 2.67 | 2.65 | 2.57 | 2.29 | 1.52 | 0.60 |
| Ethylene | 2.53 | 2.53 | 2.55 | 2.72 | 3.34 | 3.76 |
| $C_3$'s | 0.23 | 0.25 | 0.29 | 0.22 | 0.31 | 0.37 |
| Ethane conversion (%) | | N.A.* | N.A.* | 6.00 | 40.00 | 75.00 |

*conversion too low to obtain an accurate number

EXAMPLE 2

Following the method of Example 1, the reaction was run under the same conditions, but with a 5% ethane cofeed. The results are set forth in TABLE III.

TABLE III

Oxidative Coupling at 100 sccm and 1.5 atm
5% Ethane Cofeed

| Component | Feed-stream B (mole %) | Product Stream C (mole %) | | | | |
|---|---|---|---|---|---|---|
| | | 600° C. | 700° C. | 750° C. | 800° C. | 850° C. |
| Nitrogen | 0.97 | 0.95 | 0.96 | 0.96 | 0.93 | 0.89 |
| Hydrogen | 3.09 | 3.03 | 3.34 | 4.50 | 6.94 | 10.26 |
| CO | 0.64 | 0.55 | 0.55 | 0.66 | 0.67 | 0.65 |
| $CO_2$ | 2.80 | 2.75 | 2.75 | 2.75 | 2.65 | 2.54 |
| $H_2O$ | 5.43 | 7.36 | 7.25 | 5.81 | 6.88 | 7.29 |
| Methane | 77.38 | 75.87 | 75.69 | 75.90 | 73.15 | 70.62 |
| Ethane | 7.01 | 6.79 | 6.57 | 5.63 | 2.65 | 0.97 |

TABLE III-continued

Oxidative Coupling at 100 sccm and 1.5 atm
5% Ethane Cofeed

| Component | Feed-stream B (mole %) | Product Stream C (mole %) | | | | |
|---|---|---|---|---|---|---|
| | | 600° C. | 700° C. | 750° C. | 800° C. | 850° C. |
| Ethylene | 2.45 | 2.40 | 2.63 | 3.60 | 5.28 | 6.33 |
| $C_3$'s | 0.21 | 0.30 | 0.27 | 0.21 | 0.31 | 0.46 |
| Ethane Conversion (%) | | 1.00 | 5.00 | 19.00 | 61.00 | 85.00 |

EXAMPLE 3

Following the process of Example 2, using a 10% ethane cofeed, the following results, set forth in TABLE IV, were obtained.

TABLE IV

Oxidative Coupling at 100 sccm and 1.5 atm
10% Ethane Cofeed

| Component | Feed-stream B (mole %) | Product Stream C (mole %) | | | | |
|---|---|---|---|---|---|---|
| | | 600° C. | 700° C. | 750° C. | 800° C. | 850° C. |
| Nitrogen | 0.93 | 0.98 | 1.00 | 0.94 | 0.91 | 0.86 |
| Hydrogen | 2.96 | 2.96 | 3.50 | 5.55 | 9.19 | 13.35 |
| CO | 0.56 | 0.55 | 0.59 | 0.54 | 0.61 | 0.64 |
| $CO_2$ | 2.70 | 2.68 | 2.67 | 2.62 | 2.50 | 2.40 |
| $H_2O$ | 4.84 | 5.25 | 5.01 | 5.26 | 5.34 | 5.17 |
| Methane | 74.49 | 74.11 | 73.77 | 72.03 | 69.38 | 67.13 |
| Ethane | 10.91 | 10.84 | 10.35 | 8.22 | 4.46 | 1.32 |
| Ethylene | 2.41 | 2.40 | 2.86 | 4.64 | 7.28 | 8.65 |
| $C_3$'s | 0.21 | 0.24 | 0.24 | 0.21 | 0.34 | 0.49 |
| Ethane Conversion (%) | | — | 12.00 | 25.00 | 59.00 | 87.00 |

As can be seen from the above examples and Tables, the primary reaction of ethane was dehydrogenation to ethylene. Significant ethane conversions with a corresponding high selectivity to ethylene were achieved at temperatures of from 700° to 850° C. Temperatures outside this range may be employed depending upon available equipment.

The following examples illustrate the effects of various parameters on the practice of the invention through computer simulation of a process carried out in a reactor of 5" I.D. (0.127 m) with a length of 200 m., with appropriate scale-up to the respective amounts of feed indicated in each example, and simulation of unconverted feed recycle to more accurately model the commercial application of the invention. It is to be understood, however, that the benefits and effects of the practice of the invention are largely independent of the configuration of the reactor used. Thus, the applicability and utility of the invention and the principles enunciated herein are not to be construed as limited to such a reactor configuration. A flow rate of 2000 kg/hr at 900° C. was assumed for the effluent of the oxidative coupling reactor entering into the quench reactor. At the inlet of the quench reactor this stream is instantaneously and perfectly mixed with a quench stream of known composition, temperature and flow rate. The model simulates the changes in composition and temperature from this point onwards. The quench reactor is assumed to operate at a specified constant pressure. No pressure drop is taken into account. All simulations were carried out assuming an adiabatic operation. An overall material balance model was then constructed with product recovery, purge and recycle streams to simulate a commercial facility.

EXAMPLE b 4

No Hydrocarbon Quench

Using a feed of 5,290,327 pounds of methane without a hydrocarbon quench, oxidative coupling of a 900° C. light hydrocarbon feed ( 55.36 weight percent methane, 7.58 weight percent ethylene, 2.42 weight percent ethane, 0.97 weight percent CO, 5.57 weight percent $CO_2$ and 24.56 weight percent water) a flow rate of 2000 kg/hr, a residence time of 1.3 sec. time before final quench of 874° C., yields 3,071,956 pounds of olefins and $C_4+$ hydrocarbons. Product possible from $CO_x$ reaction with $H_2$: 77,785 pounds.

EXAMPLE 5

Hydrocarbon Quench-10 wt% of

Coupling Reactor Effluent

Following the process of Example 4, a feed of 5,290,327 pounds of methane, quenched with 3,594,095 pounds of propane at 25° C., yields 6,061,966 pounds of olefins and $C_4+$ hydrocarbons when reacted in an oxidative coupling unit under a pressure of 1.5 atm., a reaction effluent temperature of 900° C., a time before final quench of 1.4 seconds, a stream temperature at the time of final quench of 760° C. and employing 3,594,095 pounds of propane at 25° C. as the quenching agent. Product possible from $CO_x$ reaction with $H_2$: 255,932 pounds.

EXAMPLE 6-

Hydrocarbon Quench-10 wt% of

Coupling Reactor Effluent

Following the process of Example 4, with a stream temperature at time of final quench of 792° C. and a propane quench at 600° C., oxidative coupling of 5,290,327 pounds of methane, quenched with 3,365,777 pounds of propane, yields 6,027,064 pounds of olefins and $C_4+$ hydrocarbons. Product possible from $CO_x$ reaction with $H_2$: 265,531 pounds.

EXAMPLE 7

Hydrocarbon Quench-25 wt% of

Coupling Reactor Effluent

Under the conditions set forth in Example 6, but with 13,728,508 pounds of propane quench and 5,290,327 pounds of methane, a yield of 14,526,609 pounds of olefins and $C_4+$ hydrocarbons are obtained. Product possible from $CO_x$ reaction with $H_2$: 776,663 pounds.

EXAMPLE 8

Ethane Quench-10 wt % of

Coupling Reactor Effluent

Under the conditions set forth in Example 7, but using 3,984,128 pounds of ethane at 25° C. and a stream temperature at time of final quench of 748° C., 5,290,327 pounds of methane and 3,984,128 pounds of ethane are converted to 6,086,762 pounds of olefins and $C_4+$ hydrocarbons. Product possible from $CO_x$ reaction with $H_2$: 421,839 pounds.

EXAMPLE 9

Propane Quench-10 wt% of Coupling Reactor Effluent

Increasing the pressure to 5 atm, and using a time before final quench of 4.5 seconds, a reaction effluent temperature of 900° C., a propane quench at 25° C. and a stream temperature at time of final quench of 755° C., the oxidative coupling of 5,290,327 pounds of methane, quenched with 3,357,749 pounds of propane yields 6,033,739 pounds of olefins and $C_{4+}$ hydrocarbons. Product possible from $CO_x$ reaction with $H_2$: 244,389 pounds.

Example 4 illustrates that some temperature reduction can be accomplished as alkanes formed in the oxidative coupling reaction undergo endothermic dehydrogenation and cracking.

A comparison of Examples 4 and 5 shows that, using a propane quench at a rate of 10% of the coupling reactor effluent results in a reduction in the temperature of the combined product stream of 114° C., an increase in directly produced $C_{2+}$ olefins and $C_{4+}$ hydrocarbons of almost 100%, and an increase in the availability of $H_2$ to allow the production of about 230% more $CO_x$ derived product.

A comparison of Examples 5 and 6 show that, using a propane quench at a rate of 10% of the coupling reactor effluent, but preheating the propane to 600° C. rather than 25° C. results in an increase in the temperature of the combined product stream of 18° C. in 1.3 seconds, and about the same level of direct and indirect product manufacture.

A comparison of Examples 6 and 7 shows that, using a propane quench at a rate of 25% of the coupling reactor effluent rather than 10% results in a reduction in the temperature of the combined product stream of 57° C. in 1.3 seconds, an increase in directly produced $C_{2+}$ olefins and $C_{4+}$ hydrocarbons of almost 140%, and an increase in the availability of $H_2$ to allow the production of about 200% more $CO_x$ derived product.

A comparison of Examples 5 and 8 shows that, using ethane instead of propane as a quench at a rate of 10 weight percent of the coupling reactor effluent results in a reduction of temperature of the combined product stream of an additional 10° C. in 1.3 seconds, about the same level of directly produced $C_{2+}$ olefins and $C_{4+}$ hydrocarbons, and an increase in the availability of $H_2$ to allow the production of about 65% more $CO_x$ derived product.

A comparison of Examples 5 and 9 shows that, increasing the pressure of the system from 1.5 to 5 atmospheres results in a slight increase in temperature decline and a slight decrease of both directly produced and potential $CO_x$ derived product.

It will be understood by those skilled in the art that the optimum amount and type of quench for the particular situation, within the parameters of this invention, will be determined by local feedstock availability, markets, end products desired, and the like.

The above discussion is intended to be only illustrative of the invention. The full spirit and scope of the invention should be determined by reference to the following claims.

The invention claimed is:

1. A method for converting methane to higher molecular weight hydrocarbons comprising the steps of: reacting a methane-containing feedstock with an oxygen-containing material in a reaction zone to produce an effluent stream comprising $C_{2+}$ hydrocarbons; maintaining said effluent stream at a temperature of at least 600° C.; contacting said effluent stream with a gaseous alkane quench material having a temperature of up to 1000° C. for under 2 seconds to produce a chemically quenched effluent stream having a reduced temperature.

2. The method of claim 1 wherein the temperature of said chemically quenched stream is further reduced by thermal means to retard retrograde reactions and produce a product stream.

3. The method of claim 2 wherein said thermal means comprises recirculating refractory oils, water or a heat exchanger.

4. The method of claim 1 wherein at least a portion of said $C_{2+}$ hydrocarbons are separated and removed from unreacted methane in said chemically quenched effluent stream.

5. The method of claim 2 wherein at least a portion of said $C_{2+}$ hydrocarbons are separated and removed from unreacted methane in said product stream.

6. The method of claim 2 additionally comprising the step of recycling a recycle stream comprising a material selected from the group of at least a portion of unreacted methane in said product stream, unreacted alkane quench material, alkanes formed during said chemical quenching, and mixtures thereof to said reaction zone.

7. The method of claim 1 wherein the oxygen-containing material is in a gaseous state or is derived from a solid containing a reducible metal oxide.

8. The method of claim 1 wherein said alkane quench material comprises a $C_2-C_{20}$ alkane, and wherein said chemical quenching results in the conversion of at least a portion of the $C_2-C_{20}$ alkane quench material to alkenes with associated production of hydrogen.

9. The method of claim 1 wherein said oxygen-containing material is derived from a solid containing a reducible metal oxide, with subsequent reoxidation of said solid upon sufficient reduction thereof.

10. A method for converting a methane rich feedstock to higher molecular weight hydrocarbons comprising:
    a) reacting the feedstock with an oxygen-containing material in a reaction zone at a temperature of from 600° to 1100° C. to produce an effluent stream comprising hydrocarbons having at least 2 carbons and unreacted methane;
    (b) maintaining the temperature of said effluent stream at a temperature of at least 600° C.;
    (c) introducing a heated, gaseous alkane quench material having from 2 to 20 carbon atoms and contacting said effluent stream with said alkane quench material for up to 2 seconds thereby causing endothermic dehydrogenation of said alkane quench material and a substantial increase in $C_{2+}$ hydrocarbon products to produce an effluent product stream.

11. The method of claim 10 wherein the temperature of said chemically quenched effluent stream is further reduced by thermal means to retard retrograde reactions and produce a product stream.

12. The method of claim 11 wherein said thermal means comprises recirculating refractory oils or water.

13. The method of claim 11 wherein said thermal cooling is effected by passing said effluent stream through a heat exchanger.

14. The method of claim 10 additionally comprising the step of separating and removing $C_{2}+$ hydrocarbon products from unreacted methane in said effluent stream.

15. The method of claim 11 additionally comprising the step of separating and removing $C_{2}+$ hydrocarbon products from unreacted methane in said product stream.

16. The method of claim 11 additionally comprising the steps of separating a product stream from unreacted methane, unreacted alkane quench material and alkanes formed during chemical quenching and mixtures thereof to form a recycle stream, and recycling said recycle stream to said reaction zone.

17. The method of claim 10 wherein the oxygen containing material is in a gaseous state or is derived from a solid containing a reducible metal oxide.

18. The method of claim 10 wherein said alkane quench material is an alkane having from 2 to 5 carbon atoms.

19. The method of claim 10 wherein said alkane quench material is ethane.

20. The method of claim 10 wherein said alkane quench material is propane.

21. The method of claim 10 wherein said alkane quench material is heated to a temperature of from 500°–1000° C. prior to contact with said reaction stream.

22. The method of claim 11 wherein said alkane quench material is an alkane having from 2 to 5 carbon atoms.

23. The method of claim 11 wherein said alkane quench material is ethane.

24. The method of claim 11 wherein said alkane quench material is propane.

25. The method of claim 11 wherein said alkane quench material is heated to a temperature of from 500°–1000° C. prior to contact with said reaction stream.

26. A method for converting methane to higher molecular weight hydrocarbons comprising the steps of: reacting a methane-containing feedstock with an oxygen-containing material in a reaction zone in the presence of an oxidative coupling catalyst to produce an effluent stream comprising $C_{2}+$ hydrocarbons; maintaining said effluent stream at a temperature of at least 600° C.; contacting said effluent stream with a $C_2$–$C_{20}$ alkane quench material having a temperature of from about 500° to 1000° C. for under 2 seconds to produce a chemically quenched effluent stream having a reduced temperature; further reducing the temperature of said chemically quenched stream by thermal means to retard retrograde reactions and produce a product stream; separating and removing $C_{2}+$ products in said product stream from unreacted methane, unreacted alkane quench material, alkanes formed during chemical quenching, and mixtures thereof to form a recycle stream, and recycling said recycle stream to said reaction zone.

27. The process of claim 26 wherein said alkane quench material is an alkane having form 2 to 5 carbon atoms.

28. The process of claim 26 wherein said alkane quench material is ethane.

29. The process of claim 26 wherein said alkane quench material is propane.

* * * * *